(12) United States Patent
Aamodt et al.

(10) Patent No.: US 7,556,886 B2
(45) Date of Patent: Jul. 7, 2009

(54) HINGED ELECTRODE CUP AND METHODS OF FABRICATION FOR MEDICAL GRADE ELECTROCHEMICAL CELLS

(75) Inventors: Paul B. Aamodt, Richfield, MN (US); Karl E. Hokanson, Coon Rapids, MN (US); Stephanie L. Breimon, Delano, MN (US)

(73) Assignee: Medtronic, Inc., Minneapolis, MN (US)

( * ) Notice: Subject to any disclaimer, the term of this patent is extended or adjusted under 35 U.S.C. 154(b) by 233 days.

(21) Appl. No.: 11/096,387

(22) Filed: Mar. 31, 2005

(65) Prior Publication Data
US 2006/0222939 A1 Oct. 5, 2006

(51) Int. Cl.
*H01M 2/02* (2006.01)
(52) U.S. Cl. ............... 429/163; 429/164; 429/176; 429/246; 429/233; 429/231.95; 429/254; 429/255
(58) Field of Classification Search ............... 429/163, 429/164, 176, 245, 233, 231.95, 254, 255
See application file for complete search history.

(56) References Cited
U.S. PATENT DOCUMENTS

| 4,863,815 | A | | 9/1989 | Chang et al. |
| 5,439,760 | A | * | 8/1995 | Howard et al. ............... 429/94 |
| 5,458,997 | A | | 10/1995 | Crespi et al. |
| 5,486,215 | A | | 1/1996 | Kelm et al. |
| 5,549,717 | A | | 8/1996 | Takeuchi et al. |
| 5,616,429 | A | | 4/1997 | Klementowski |
| 5,681,668 | A | * | 10/1997 | Reed et al. ............... 429/100 |
| 5,744,261 | A | | 4/1998 | Muffoletto et al. |
| 6,040,082 | A | | 3/2000 | Haas et al. |
| 6,667,129 | B2 | * | 12/2003 | Chikada ............... 429/99 |
| 2005/0118501 | A1 | * | 6/2005 | Hashimoto et al. ............... 429/180 |
| 2005/0142439 | A1 | * | 6/2005 | Lee et al. ............... 429/163 |

FOREIGN PATENT DOCUMENTS

EP 1053763 A 11/2000

* cited by examiner

*Primary Examiner*—Jane Rhee (57) ABSTRACT

According to the present invention an improved insulator cup, or case liner, enhances electrode coil insertion by reducing the possibility of damage to the coil during insertion, protects electrode and separator from laser radiation during welding, and eases manual inspection of partially assembled components, among other advantages. The improved insulator cup includes a mechanical joint, or hinge-like feature, which pivotably couples opposing parts of the cup and greatly enhances coiled electrode insertion and subsequent component inspection prior to sealing a cover member over an electrode assembly disposed within a housing. The mechanical joint can comprise additional parts that adhere to a divided insulator cup or can be formed as an integral part of an insulator cup (e.g., a linear area of reduced thickness, of apertures, and/or perforations, etc.).

22 Claims, 9 Drawing Sheets

HINGED ELECTRODE CUP AND METHODS OF FABRICATION FOR MEDICAL GRADE ELECTROCHEMICAL CELLS

FIELD OF THE INVENTION

The present invention relates to electrochemical cells; in particular, apparatus and methods for fabricating medical grade electrochemical cells for implantable medical devices (IMDs).

BACKGROUND OF THE INVENTION

The invention relates primarily to coiled electrode type electrochemical cells. For example, a coil of an active material such as lithium (for an anode) is placed in an insulator cup formed of a polymer material prevents direct contact between the lithium anode and the typically metallic housing for the cell as well as the cathode active material.

Unfortunately, the coiled electrode and the insulator cup itself are designed to occupy minimum space within the cell and thus possess dimensions that oftentimes result in damage during manual assembly. For example, the coiled electrode oftentimes includes a commercially available separator sheet or envelope around the electrode and the sheet easily sustains damage. Also, the coil itself can be damaged (e.g., deformed or squeezed, cut or torn) when it is inserted through upper edges of an open metallic housing.

Thus, the anode subassembly is essentially complete and can be combined with suitable electrolyte and cathode within a sealed enclosure, which for medical devices is typically formed of titanium, stainless steel or the like.

Inherently, the traditional process just described is labor intensive, with discrete variable highly controlled processing requiring the full attention and effort of anode fabrication engineers. Because the coiled electrode is inserted into an essentially opaque cup inspection of the partially or fully assembled electrochemical cell is oftentimes limited to electrical inspection or interrogation.

Thus, a need exists in the art to improve fabrication of coiled electrodes to improve the ability to fully inspect the partially assembled components and to decrease costs, process steps and lot variability with a concomitant increase in manufacturing yield, consistency, quality and performance of the resulting electrochemical cell.

SUMMARY OF THE INVENTION

According to the present invention an improved insulator cup, or case liner, enhances electrode coil insertion by reducing the possibility of damage to the coil during insertion, protects electrode and separator from laser radiation during welding, and eases manual inspection of partially assembled components, among other advantages.

The improved insulator cup includes a mechanical joint, or hinge-like feature, which pivotably couples opposing parts of the cup and greatly enhances coiled electrode insertion and subsequent component inspection prior to sealing a cover member over an electrode assembly disposed within a housing. The mechanical joint can comprise additional parts that adhere to a divided insulator cup or can be formed as an integral part of an insulator cup (e.g., a linear area of reduced thickness, of apertures, and/or perforations, etc.).

The improved insulator cup optionally includes one or more apertures for operatively receiving electrical tab members that couple to the coiled electrodes (i.e., a negative anode electrode and a positive cathode electrode).

An improved insulator cup according to the invention can be fabricated using a number of techniques, including injection molding or the like, and the hinge-like feature can comprise a scribe line, a prefabricated slit, a molded break line or the like. The hinge-like feature can reside in the longitudinal axis or the lateral (or axial) axis of a cup fabricated according to the invention. The chosen location for the feature can be dictated by the shape of the electrochemical cell housing and the location of any electrical connection tabs extending therefrom. For example, it depends upon whether the housing comprises a substantially prismatic so-called shallow drawn housing (having a cover opposing a largest major surface) or a deep drawn housing (having a cover opposing a smaller surface such as a small bottom surface).

The insulator cup according to the invention can utilize a wide variety of materials such as carbon black ETFE, substantially clear resin-based material or partially opaque materials and the like. The cup can extend partially into the full depth of the electrochemical housing (e.g., can provide insulation and protection to only one end or part of one end of a coiled electrode). Alternatively, a pair of opposing cup members according to the invention can be used to envelop a coil from opposing ends or sides. In this aspect of the invention, an overlapping section between the opposing cups can be utilized. In another aspect of the invention in addition to at least one cup formed and implemented according to the invention, a dielectric spacer member or plate can be disposed between the electrode and the typically metallic housing on a side of a cell not occupied by the cup member.

In one form of the invention, a resin-based, pre-dimensioned electrode cup has a substantially or completely enclosed sidewalls and a major opening opposing a major surface and the major surface includes a longitudinal hinge-like feature. With the cup hinge disposed in an open configuration a coiled electrode is inserted into the cup, the hinge closed, and the electrode/cup subassembly inserted into the major opening of the electrochemical cell housing. In a shallow-drawn cell housing the major surface abuts the cover thus providing thermal and optical insulation from laser radiation when the cover for the cell is laser welded onto the shallow drawn casing. Thus, according to the invention visible inspection can be performed quickly and easily and the likelihood of damage to the coil when inserting it into the housing and during laser welding is greatly diminished.

With respect to a current collector element, a solid, screen, slotted, or perforated metallic member may be used over all or a portion of the length of the coiled electrode (e.g., an elongated piece of lithium). In one embodiment of the invention two cathode current collector tabs extend out of the periphery of the coiled electrodes and through preformed tab apertures and a single anode tab extends from a single anode current collector. In this form of the invention, the current collectors comprise titanium, are devoid of apertures and are accompanied by at least one resin-based spacer member for at least one turn of the electrode coil assembly.

With regard to the cup any appropriately electrically insulative material can be utilized (e.g., polypropylene, rubber, extruded or molded thermoplastic, and the like). The material should be suitably resilient so that it withstands compression while maintaining its shape for final insertion into a housing for an electrochemical cell. The cup can be adapted to conform to any arbitrary shape including curves, angled surfaces, dimpled surfaces and the like although substantially prismatic shapes are most often utilized.

The inventive family of cups according to the invention are primarily described and depicted with respect to coiled electrodes but can also be used for diverse types of electrochemical cells, including in particular to flat plate primary batteries as well as secondary cells.

The following drawings are not drawn to scale and common reference numerals are utilized to refer to like elements throughout the written description. Of course, the invention is not limited to the illustrate embodiments but rather only by the appended claims which define the literal metes and bounds of the claims, and equivalents thereof.

DETAILED DESCRIPTION OF THE ILLUSTRATED EMBODIMENTS

Figure 1:
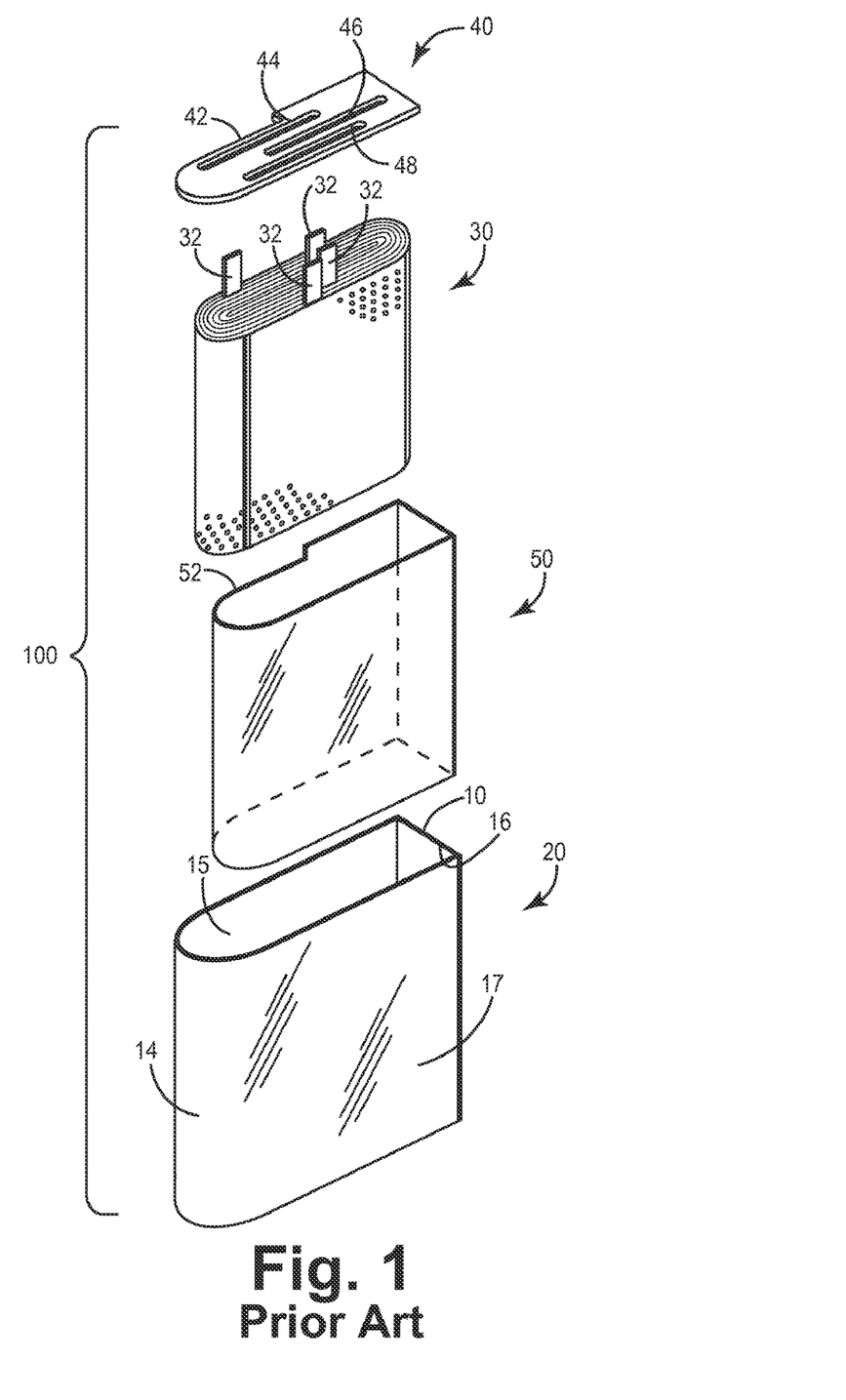
FIG. 1 depicts an exploded view of an exemplary electrochemical cell which includes an insulator cup, a cell housing and a coiled electrode assembly.

Referring now to FIG. 1, which depicts an exploded view of an exemplary prior art electrochemical cell which includes a case 20 and coiled electrode assembly 30. The case 20 is designed to enclose the electrode assembly 30 and be sealed by a case cover 60. As depicted the side 14 of the case 20 forms a generally arcuate shape while the opposing side 16 of the case 20 is preferably generally planar or prismatic. This construction provides a number of advantages including the ability to accommodate one of the curved or arcuate ends of a preferred coiled electrode assembly 30 but such a shape can be used when practicing the present invention (described hereinbelow). As also discussed below, the arcuate side 14 can nest within an arcuate edge of an implantable medical device such as an implantable cardioverter-defibrillator (ICD). When the arcuate side 14 is located within the edge of a device, the planar surface on the opposing side 16 faces inward to assist in the efficient use of space within a device case.

The details regarding construction of the electrode assembly, such as connector tabs, electrode pouches, etc., are secondary to the present invention and will be described generally below with a more complete discussion being found in, e.g., U.S. Pat. No. 5,458,997 (Crespi et al.).

The electrode assembly 30 depicted in FIG. 1 is preferably a wound or coiled structure similar to those disclosed in, e.g., U.S. Pat. No. 5,486,215 (Kelm et al.) and U.S. Pat. No. 5,549,717 (Takeuchi et al.). As a result, the electrode assemblies typically exhibit two generally planar sides, bounded by two opposing generally arcuate edges and two opposing generally planar ends. The composition of the electrode assemblies can vary, although one preferred electrode assembly includes a wound core of lithium/silver vanadium oxide (Li/SVO) battery as discussed in, e.g., U.S. Pat. No. 5,458,997 (Crespi et al.). Other battery chemistries are also anticipated, such as those described in U.S. Pat. No. 5,616,429 to Klementowski, with the preferred cores comprising wound electrodes having at least one generally semicircular or arcuate end that is adapted to nest within the arcuate side 14 of the case 20. Such a design provides a volumetrically efficient high current rate battery useful in many different implantable devices.

The electrode assembly 30 includes an anode, a cathode and a porous, electrically non-conductive separator material encapsulating either or both of the anode and cathode. These three components are preferably laminated together and wound to form the electrode assembly 30. The anode portion of the electrode assembly can comprise a number of different materials including an anode active material located on an anode conductor element. Examples of suitable anode active materials include, but are not limited to: alkali metals, materials selected from Group IA of the Periodic Table of Elements, including lithium, sodium, potassium, etc., and their alloys and inter-metallic compounds including, e.g., Li—Si, Li—B, and Li—Si—B alloys and inter-metallic compounds, insertion or intercalation materials such as carbon, or tin-oxide. Examples of suitable materials for the anode conductor element include, but are not limited to: stainless steel, nickel, titanium, or aluminum.

Referring in general to the present invention, the cathode portion of the electrode assembly includes a cathode active material located on a cathode current collector that also conducts the flow of electrons between the cathode active material and the cathode terminals of the electrode assembly 30. Examples of materials suitable for use as the cathode active material include, but are not limited to: a metal oxide, a mixed metal oxide, a metal sulfide or carbonaceous compounds, and combinations thereof. Suitable cathode active materials include without limitation carbon monofluoride (CFx), silver vanadium oxide (SVO), copper vanadium oxide, copper silver vanadium oxide (CSVO), manganese dioxide, titanium disulfide, copper oxide, copper sulfide, iron sulfide, iron disulfide, carbon and fluorinated carbon, and mixtures thereof, including lithiated oxides of metals such as manganese, cobalt, and nickel.

The cathode active material comprises a mixed metal oxide formed by chemical addition, reaction or otherwise intimate contact or by thermal spray coating process of various metal sulfides, metal oxides or metal oxide/elemental metal combinations. The materials thereby produced contain metals and oxides of Groups IB, IIB, IIIB, IVB, VB, VIIB, VIIB, and VIII of the Periodic Table of Elements, which includes noble metals and/or their oxide compounds.

The cathode active materials can be provided in a binder material such as a fluoro-resin powder, preferably polytetrafluoroethylene (PTFE) powder that also includes another electrically conductive material such as graphite powder, acetylene black powder and carbon black powder. In some cases, however, no binder or other conductive material is required for the cathode.

The separator material electrically insulates the anode from the cathode. The material is preferably wettable by the cell electrolyte, sufficiently porous to allow the electrolyte to flow through the separator material, and maintain physical and chemical integrity within the cell during operation. Examples of suitable separator materials include, but are not limited to: ceramics, non-woven glass, polyethylenetetrafluoroethylene, glass fiber material, polypropylene, and polyethylene.

The electrode assembly 30 is inserted into an electrically non-conductive case liner 50. The case liner 50 extends at its top edge above the edge of the electrode assembly 30 to overlap with other electrically non-conductive elements. If the case liner 50 does extend above the electrode assembly 30, it can include a notch 52 on one side to allow for the connection between one set of the connector tabs 32 to the case 20. The electrode assembly 30, coil insulator 40 and case liner 50 are then preferably inserted into the case 20. Insertion of the electrode assembly 30 into case 20 is performed manually, and as depicted in FIG. 1, a coil insulator 40 is placed on the electrode assembly 30. The coil insulator 40 includes a notch 42 to accommodate one of the connector tabs 32 on the electrode assembly 30 and slits 44,46 and 48 to accommodate other connector tabs 32.

Figure 2:
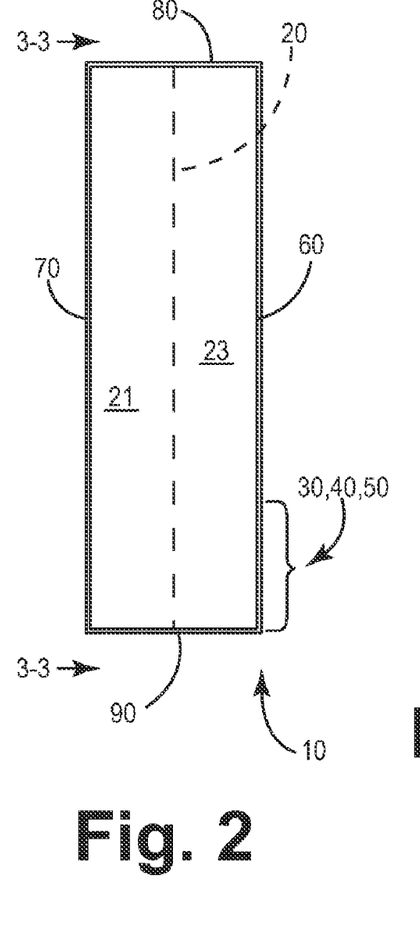
FIG. 2 is a plan view of an embodiment of an insulator cup according to the invention.
Figure 4:
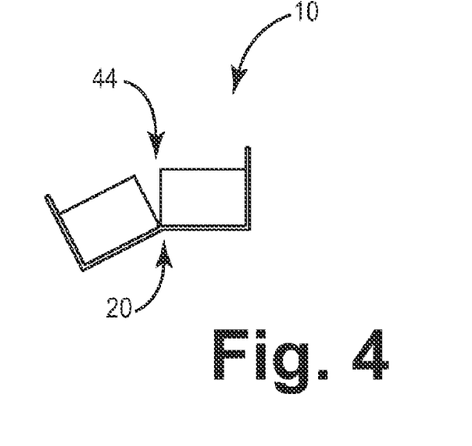
FIG. 4 schematically depicts a hinged insulator cup according to the invention wherein the hinge is at least partially open thus resulting in an enlarged major opening of the cup.
Figure 5:
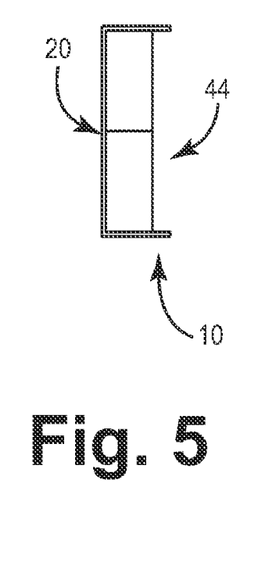
FIG. 5 schematically depicts a hinged insulator cup according to the invention wherein the hinge is essentially closed thus reducing the major opening of said cup.

Now referring to FIG. 2, a plan view of an embodiment of an insulator cup 10 according to the invention, an axial fold line or hinge location (depicted by reference numeral 20) divides portions 21,23 of a major surface of the cup 10. As shown in FIGS. 4 and 5, the portions 21,23 opposing major opening 44 of the cup 10. Although the fold line 20 depicted in FIG. 2 is shown centered between portions 21,23 but no such limitation exists as the fold line 20 can be implemented axially or laterally in virtually any location of the major surface. Sidewall portions 60,70,80,90 surround the major surface and while not specifically depicted apertures 30,40,50 are formed in a portion of sidewall 60.

Figure 3:
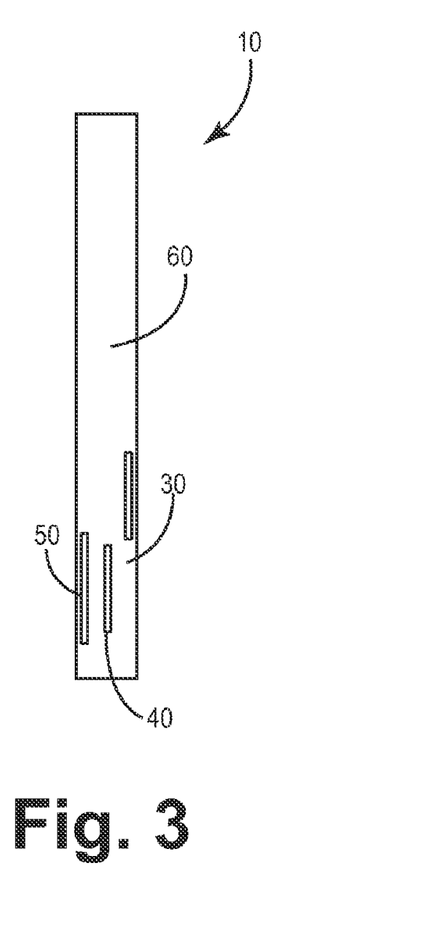
FIG. 3 is an elevational side view of an inventive insulator cup depicting an embodiment having three apertures for admitting conductive tabs that couple to electrodes within the coiled electrode assembly.
Figure 12:
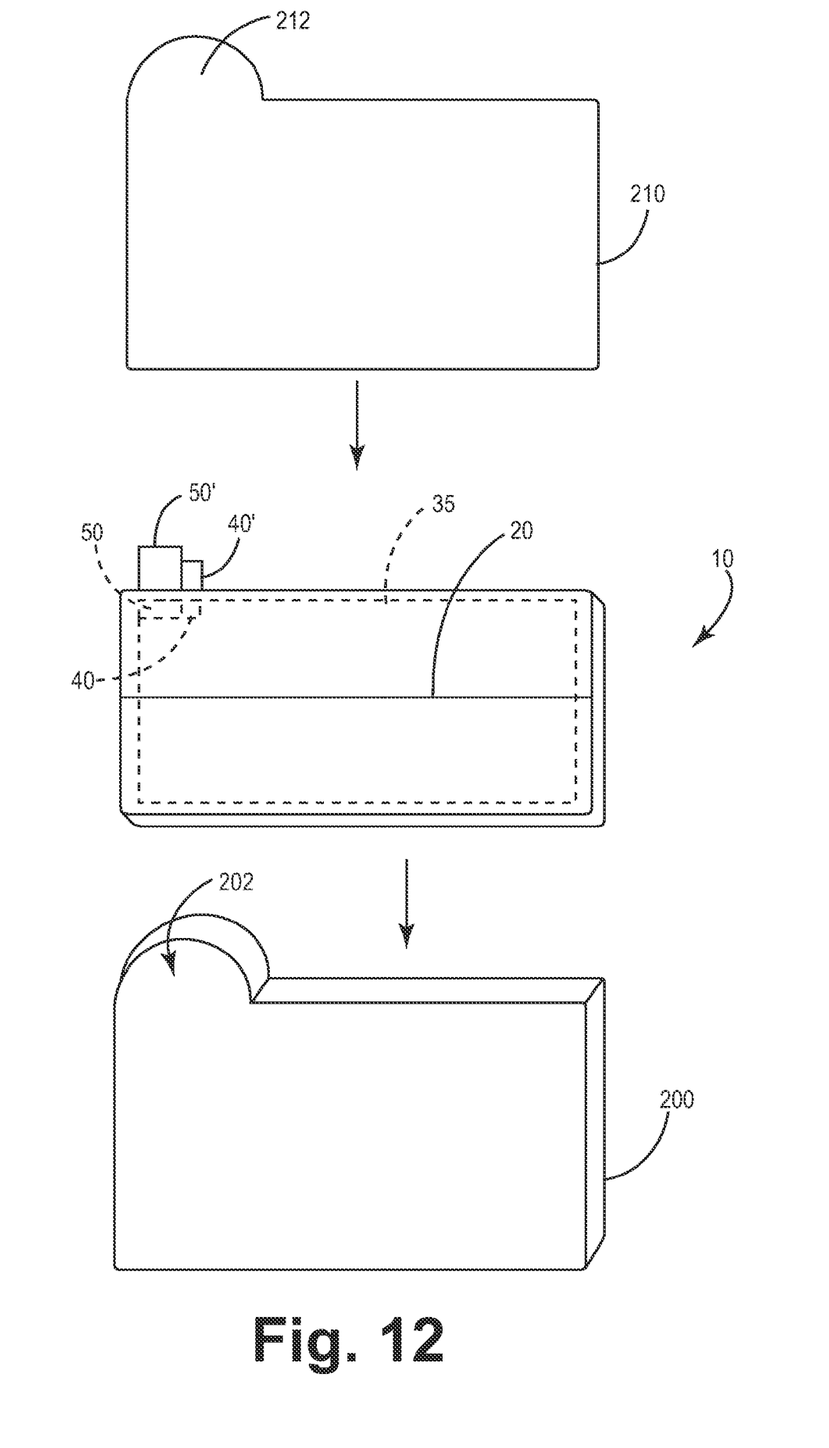
FIG. 12 is an exploded view of an insulator cup according to the invention with an electrode assembly disposed therein (shown in ghost) having tabs extending through apertures poised between a housing and a corresponding housing cover member.

In FIG. 3, an elevational side view of an inventive insulator cup 10, an embodiment having three apertures 30,40,50 formed in sidewall 60 for admitting conductive tabs (not depicted) that couple to electrodes within the coiled electrode assembly (see 30 in FIG. 1, and 35 in FIG. 12). While three apertures are depicted, more or less (including zero) apertures can be used when practicing the present invention depending on the cell housing shape and whether a cell is case-neutral, case-positive, or case-negative.

FIG. 4 schematically depicts a hinged insulator cup 10 according to the invention wherein the hinge location 20 is at least partially open thus resulting in an enlarged major opening 44 of the cup 10.

FIG. 5 schematically depicts a hinged insulator cup 10 according to the invention wherein the hinge (at location 20) is essentially closed thus reducing the major opening 44 of said cup 10 from the configuration depicted in FIG. 4.

Figure 6:
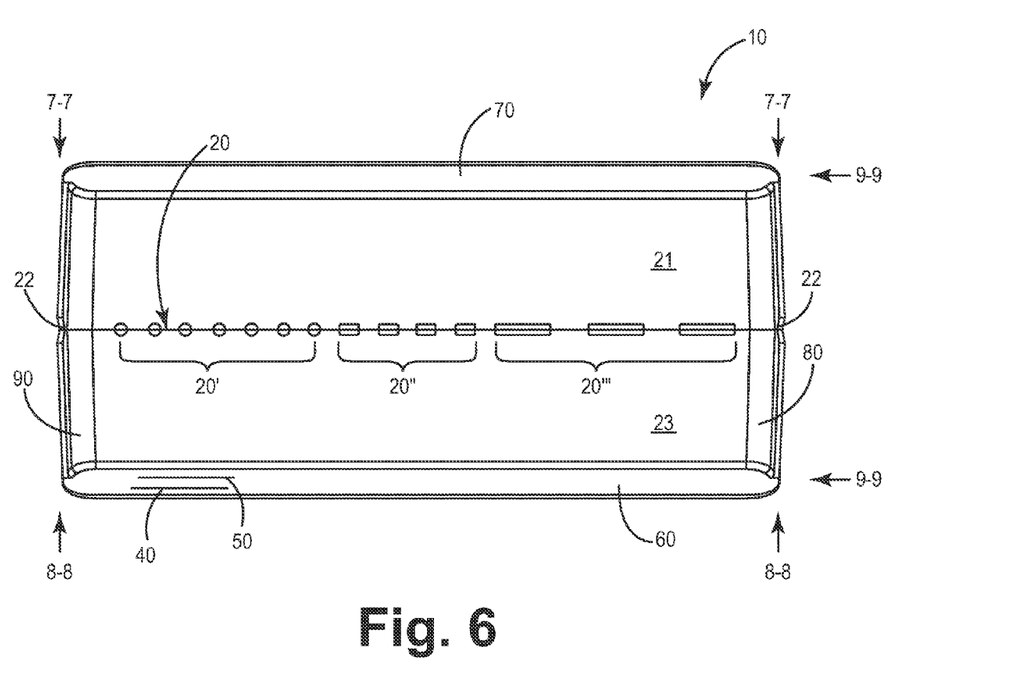
FIG. 6 is a perspective view of a hinged insulator cup according to the invention wherein the hinge is substantially closed (as schematically depicted in FIG. 5).

FIG. 6 is a perspective view of a hinged insulator cup 10 according to the invention wherein the hinge location 20 is substantially closed (as schematically depicted in FIG. 5). As mentioned previously, the fold line (or hinge location) 20 can comprise many different surface features and/or materials. For example, as depicted in FIG. 6 the fold line 20 can comprise a series of apertures 20', small linear perforations 20", and/or series of longitudinal slots 20''' and the like. In addition or in lieu of the foregoing the fold line 20 can include a continuous or substantially continuous linear region of relatively thin material. In addition, on the sidewalls 80,90 which meets the fold line 20 a pair of opposing cut outs 22 can optionally provide ease of opening and closing of the hinge 20. In use the hinge is opened and one or more conductive tabs coupled to an electrode (not depicted) are inserted from the interior of the cup 10 through one of the apertures 40,50 formed in sidewall 60. The electrode is seated in the cup and the hinge is closed (i.e., major portions 21,23 are returned to a substantially coplanar orientation). Thus, an appropriately sized electrode (and connector tab(s)) is retained within the cup 10 and surrounded on three sides—by the major surface (portions 21,23) and the sidewalls (60,70,80,90). The electrode/cup assembly then can be conveniently inserted into a cell housing (20 in FIG. 1, 200 in FIG. 12) whether a shallow-drawn housing (200 in FIG. 12) or a deep-drawn housing (20 in FIG. 1). If visual inspection or confirmation of the location and condition of the electrode or other components of the inserted electrode is desired, then the hinge can be opened slightly for visual confirmation (in the case of a deep-drawn housing the assembly may need to be inspected prior to insertion or partially withdrawn from the housing). The cell housing can then be sealed by placing a cover over the open end of the cell housing and welding it to the upper periphery of the opening. In addition, although not depicted one or more layers of protective material can be placed between the electrode assembly and the interior of the cell housing. Such layer(s) of material can be initially placed in the cell housing or can be applied to the electrode/cup assembly prior to deployment into the cell housing.

Figure 7:
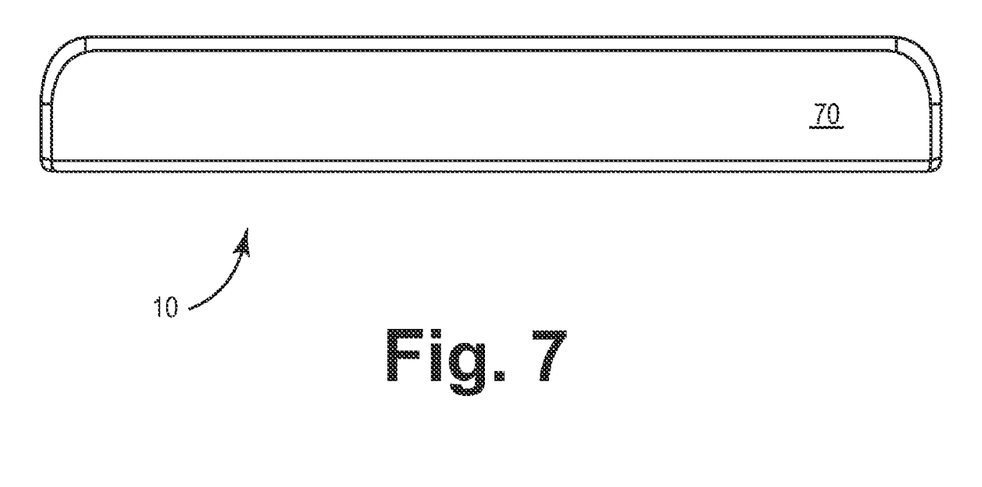
FIG. 7 is an elevational side view of an inventive insulator cup as viewed along lines 7-7 of FIG. 6.

FIG. 7 is an elevational side view of an inventive insulator cup 10 as viewed along lines 7-7 of FIG. 6 thus providing a view of the profile of one embodiment of a sidewall 70.

Figure 8:
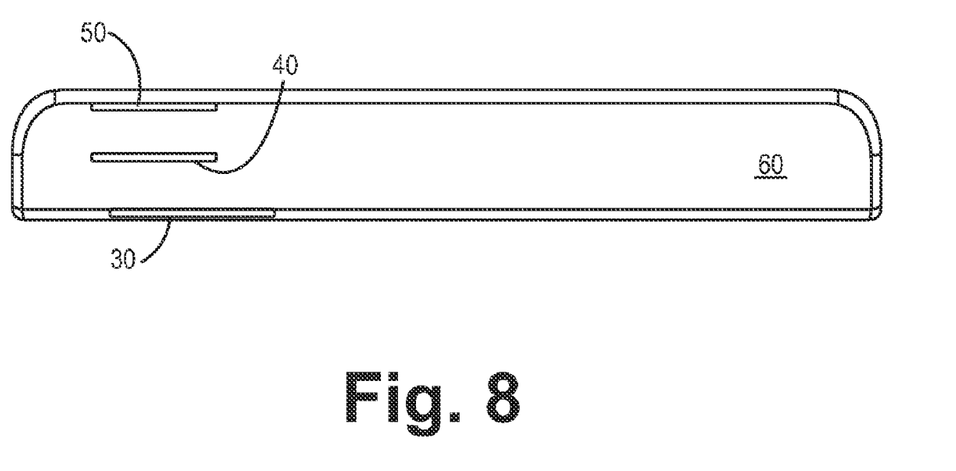
FIG. 8 is an elevational side view of an inventive insulator cup as viewed along lines 8-8 of FIG. 6.

FIG. 8 is an elevational side view of an inventive insulator cup 10 as viewed along lines 8-8 of FIG. 6 thus providing a view of the profile of one embodiment of sidewall 60 and tab-admitting apertures 30,40,50.

Figure 9:
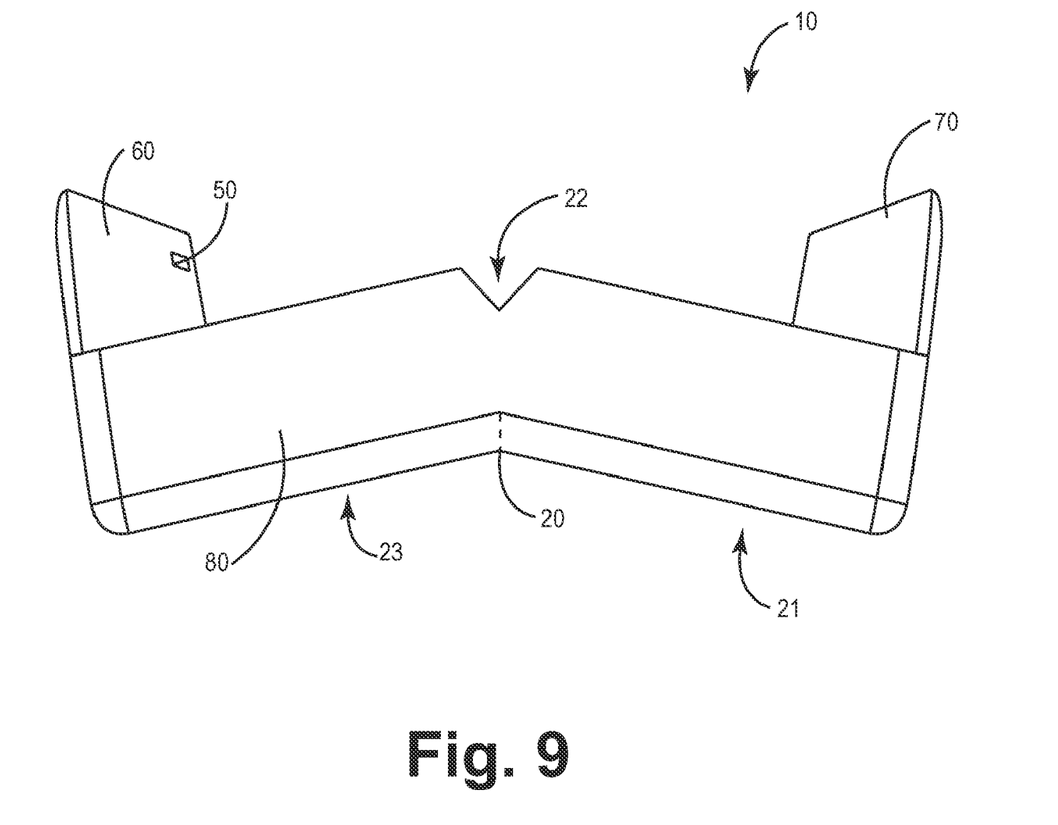
FIG. 9 is an elevational side view of an inventive insulator cup as viewed along lines 9-9 of FIG. 6.

FIG. 9 is an elevational side view of an inventive insulator cup 10 as viewed along lines 9-9 of FIG. 6 thus providing a view of the profile of sidewall 80, fold line 20 and hinge-movement feature 22 and sidewalls 60,70 and tab-admitting aperture 50. The cup 10 depicted in FIG. 9 is oriented slightly open (i.e., portions 21,23 are substantially non-coplanar). In addition, while not depicted, the material between feature 22 and fold line 20 can also include an opening, slot, perforation or the like to assist opening the cup 10 for insertion of an electrode.

Figure 10:
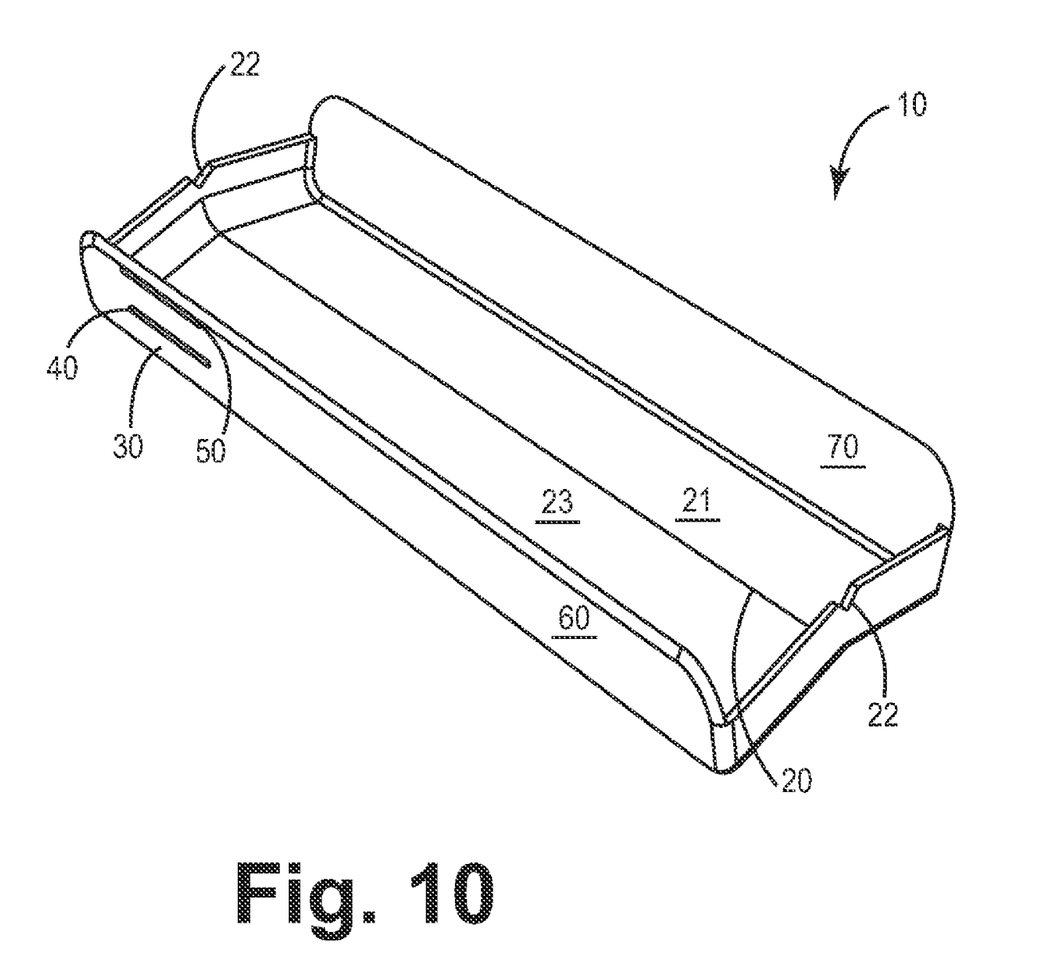
FIG. 10 is a perspective line drawing view of an embodiment of a hinged insulator cup according to the invention.

FIG. 10 is a perspective line drawing view of an embodiment of a hinged insulator cup 10 according to the invention in the configuration depicted in FIG. 9. The lines depicted in FIG. 10 connote a location of a radius or intersecting planes for various surfaces. Apertures 30,40,50 extend through sidewall 60 and portions 21,23 are divided by fold line 20 and fold line 20 extends nearly all the way toward end-features 22.

Figure 11:
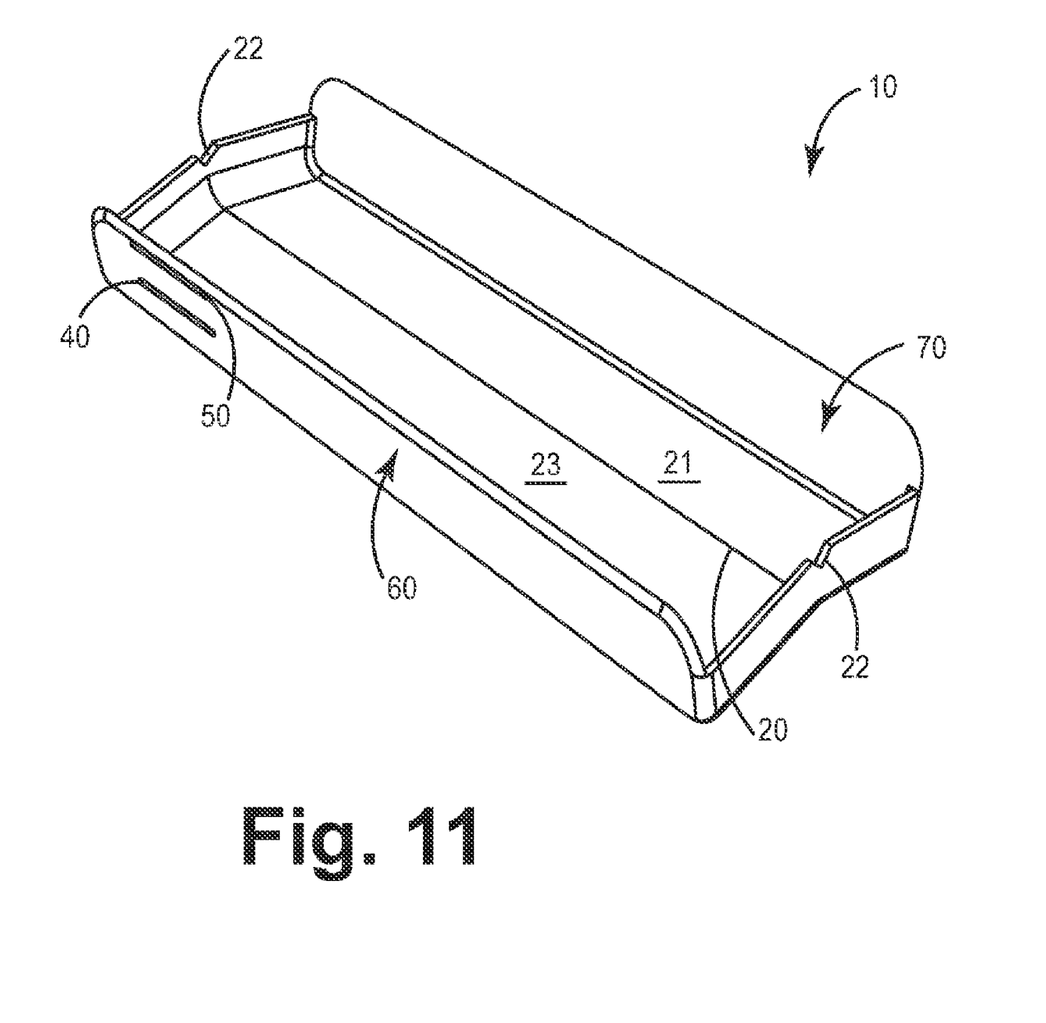
FIG. 11 is a perspective solid view of the embodiment of the hinged insulator cup depicted in the line drawing of FIG. 10.

FIG. 11 is a perspective solid view of the embodiment of the hinged insulator cup depicted in the line drawing of FIG. 10.

FIG. 12 is an exploded view of an insulator cup 10 according to the invention with an electrode assembly disposed therein (shown in ghost) having tabs 40',50' extending through apertures 40,50 poised between a housing 200 and a corresponding housing cover member 210. The housing 200 includes a headspace area 202 providing room within the cell housing 200 for the tab members 40',50' which area 202 is covered by a corresponding portion 212 of cover 210 following assembly of a cell according to the invention. Two unnum- The invention has been described with reference to a few discrete embodiments but is not to be construed as so limited. As those of skill in the art appreciate the various components of the invention can be substituted or modified slightly without departing from the scope of the invention herein disclosed. Indeed, the invention is defined by the appended claims, which define the true metes and bounds thereof, as well as equivalents thereof.

The invention claimed is:

1. An implantable medical device containing an electrochemical cell, comprising:
    an electrochemical cell comprising
    a case;
    a case liner disposed within the case, the case liner having a first cup portion fabricated from electrically non-conductive material and a second cup portion fabricated from electrically non-conductive material;
    said first and second cup portions of the case liner having side walls which together form a wall edge that circumscribes an opening to an interior space within the case liner;
    a hinge coupling the first and second cup portions to provide for articulation between them;
    said case liner having a major lower surface opposing the opening, the hinge formed along the major lower surface; and
    a volume of electrode material disposed within the interior of the case liner; and
    the electrochemical cell disposed within an implantable medical device.

2. An implantable medical device according to claim 1, wherein the hinge comprises one of: a crease, a scribe line, a linear series of perforations, and an elongated slot.

3. An electrochemical cell according to claim 1, wherein the electrode material further comprises a coiled member.

4. An implantable medical device according to claim 3, wherein the coiled member comprises a lithium material.

5. An implantable medical device according to claim 1, further comprising a current collector embedded within a portion of the lithium material.

6. An implantable medical device according to claim 5, wherein the current collector comprises a substantially solid sheet of metal.

7. An implantable medical device according to claim 5, wherein the current collector comprises at least one of a nickel material and a copper material.

8. An implantable medical device according to claim 5, wherein the current collector comprises one of a substantially planar and at least one elongated member.

9. An implantable medical device according to claim 8, wherein the substantially planar current collector has at least one aperture formed therein.

10. An implantable medical device according to claim 5, wherein the current collector is disposed in at least one of the following locations: a lower surface of the case liner, an intermediate location between the opening and the lower surface of the case liner, abutting a side wall of the case liner.

11. An implantable medical device according to claim 5, wherein the current collector further comprises an electrical tab coupled to a portion of the current collector and extending through the case liner via one of: a side wall and a lower surface.

12. An implantable medical device according to claim 1, wherein the case liner is fabricated from one of: a resin-based material, a thermoformed material, an injection-molded material.

13. An implantable medical device according to claim 1, wherein the case liner is fabricated of a polyolefin material.

14. An implantable medical device according to claim 1, wherein the case liner is fabricated of one of: a polypropylene material and a polyethylene material.

15. An implantable medical device according to claim 1, wherein the case liner is configured as one of a prismatic shaped vessel and a vessel having at least one substantially curved portion.

16. An implantable medical device according to claim 1, wherein the volume of electrode material comprises a lithium material.

17. An implantable medical device according to claim 1, wherein the opening opposing and the major lower surface each configured into one of: a square shape, a rectangular shape, a triangular shape, an ovoid shape, a round shape.

18. An implantable medical device according to claim 1, further comprising a portion of separator material disposed between opposing electrodes.

19. An implantable medical device according to claim 1, wherein the separator material comprises one of: a Kraft paper material, a cellulose material, a perforated polypropylene material, a perforated polyurethane material, a non-woven material.

20. An electrochemical cell according to claim 1, wherein the hinge having a closed position corresponding to the opening being circumscribed by the wall edge.

21. An implantable medical device containing an electrochemical cell, comprising:
    a case;
    a case liner disposed within the case, the case liner having a lower major surface and an opposing open side forming an opening to an interior space within the case liner, the case liner comprising a first cup portion fabricated from electrically non-conductive material and a second cup portion fabricated from electrically non-conductive material;
    said first and second cup portions of the case liner each having a lower surface portion, said lower surface portions together forming the lower major surface;
    said first and second cup portions each having a side wall extending upward from the major lower surface, said side walls together forming a wall edge that circumscribes the opposing open side;
    a hinge formed along the lower major surface for coupling the first and second cup portions and for providing articulation between them, the hinge having a closed position corresponding to the opposing open side being circumscribed by the side walls of the first and second cup portions;
    means aligned with the hinge for allowing the hinge to move to an open position to move the side walls of the first and second cup portions away from each other and enlarging the opening; and
    a volume of electrode material disposed within the interior of the case liner; and
    the electrochemical cell disposed within an implantable medical device.

22. The implantable medical device of claim 21 wherein the hinge comprises one of: a scribe line, a linear series of perforations, and an elongated slot.

* * * * *